(12) United States Patent
Wang et al.

(10) Patent No.: US 9,033,883 B2
(45) Date of Patent: May 19, 2015

(54) FLOW QUANTIFICATION IN ULTRASOUND USING CONDITIONAL RANDOM FIELDS WITH GLOBAL CONSISTENCY

(71) Applicants: Yang Wang, Princeton, NJ (US); Bogdan Georgescu, Plainsboro, NJ (US); Saurabh Datta, Pleasanton, CA (US)

(72) Inventors: Yang Wang, Princeton, NJ (US); Bogdan Georgescu, Plainsboro, NJ (US); Saurabh Datta, Pleasanton, CA (US)

(73) Assignee: Siemens Corporation, Iselin, NJ (US)

( * ) Notice: Subject to any disclaimer, the term of this patent is extended or adjusted under 35 U.S.C. 154(b) by 240 days.

(21) Appl. No.: 13/682,272

(22) Filed: Nov. 20, 2012

(65) Prior Publication Data

US 2013/0144161 A1    Jun. 6, 2013

Related U.S. Application Data

(60) Provisional application No. 61/562,563, filed on Nov. 22, 2011.

(51) Int. Cl.
| | |
|---|---|
| *A61B 8/00* | (2006.01) |
| *A61B 8/06* | (2006.01) |
| *A61B 8/08* | (2006.01) |
| *G01S 15/89* | (2006.01) |

(52) U.S. Cl.
CPC .............. *A61B 8/065* (2013.01); *A61B 8/0883* (2013.01); *A61B 8/483* (2013.01); *A61B 8/488* (2013.01); *A61B 8/5269* (2013.01); *G01S 15/8981* (2013.01)

(58) Field of Classification Search
CPC ...... A61B 8/065; A61B 8/5269; A61B 8/483; A61B 8/488; G01S 15/8981
USPC ......................................................... 600/438
See application file for complete search history.

(56) References Cited

PUBLICATIONS

S. H. Little, MD, Quantifying Mitral Valve Regurgitation: New Solutions from the $3^{rd}$ Dimension, JASE 23(1), pp. 9-12, 2010.
A. A. Pellett, Ph.D. et al., "Doppler Aliasing," Echocardiography 22, pp. 540-542, 2005.
L. Hatle et al., "Doppler Ultrasound in Cardiology: Physical Principles and Clinical Applications," Lea & Febinger, 1993.
T. R. Skaug et al., "Quantification of Mitral Regurgitation Using High Pulse Repetition Frequency Three-Dimensional Color Doppler," JASE 23(1), pp. 1-8, 2010.
W. A. Zoghbi et al., "Recommendations for Evaluation of the Severity of Native Valvular Regurgitation with Two-dimensional and Doppler Echocardiography," JASE 16(7), pp. 777-802, 2003.
Y. Matsumara, MD, et al., "Geometry of the proximal isovelocity surface area in mitral regurgitation by 3-dimensional color Doppler echocardiography: Difference between functional mitral regurgitation and prolapse regurgitation," American Heart Journal 155(2), pp. 231-238, 2008.

(Continued)

*Primary Examiner* — Bo J Peng

(57) ABSTRACT

Velocities are unaliased using conditional random fields. To constrain the energy minimization function, a global term includes a measure of a level of aliasing. In one example, the measure of the level of aliasing is based on a change in volume, such as the volume of the left ventricle. The unaliasing is performed along one or more surfaces, such as surfaces intersecting the mitral annulus and the left ventricle outflow tract. The anatomy used is identified and/or tracked using one or more machine-learnt detectors. Both B-mode and velocity information may be used for detecting the anatomy.

13 Claims, 3 Drawing Sheets

(56) References Cited

PUBLICATIONS

C. Yosefy, MD, et al., "Proximal Flow Convergence Region as Assessed by Real-time 3-Dimensional Echocardiography: Challenging the Hemispheric Assumption," JASE 20(4), pp. 389-396, 2007.

B. Picht, MD, et al., "Direct Quantification of Mitral Regurgitant Flow Volume By Real-Time Three-Dimensional Echocardiography Using Dealiasing of Color Doppler Flow at the Vena Contracta," JASE 21(12), pp. 1337-1346, 2008.

S. Muth et al., "Unsupervised dealiasing and denoising of color-Doppler data," Medical Image Analysis, 15, pp. 577-588, 2011.

J. Lafferty et al., "Conditional Random Fields: Probabilistic Models for Segmenting and Labeling Sequence Data," In: ICML, pp. 1-8, 2001.

J. M. Gonfaus et al., "Harmony Potentials for Joint Classification and Segmentation," In: CVPR, pp. 3280-3287, 2010.

Y. Zheng et al., "Four-Chamber Heart Modeling and Automatic Segmentation for 3D Cardiac CT Volumes Using Marginal Space Learning and Steerable Features," IEEE TMI 27(11), pp. 1-14, 2008.

Y. Wang et al., "Automatic Cardiac Flow Quantification of 3D Volume Color Doppler Data," In: ISBI, pp. 1688-1691, 2011.

D. Comaniciu et al., "Mean Shift: A Robust Approach Toward Feature Space Analysis," IEEE PAMI 24(5), pp. 603-619, 2002.

Z. Tu, "Probabilistic Boosting-Tree: Learning Discriminative Models for Classification, Recognition, and Clustering," In: ICCV, pp. 1589-1596, 2005.

FLOW QUANTIFICATION IN ULTRASOUND USING CONDITIONAL RANDOM FIELDS WITH GLOBAL CONSISTENCY

RELATED APPLICATIONS

The present patent document claims the benefit of the filing date under 35 U.S.C. §119(e) of Provisional U.S. Patent Application Ser. No. 61/562,563, filed Nov. 22, 2011, which is hereby incorporated by reference.

BACKGROUND

The present embodiments relate to flow quantification in ultrasound imaging.

Valvular heart diseases are a significant cause of morbidity and mortality. The quantification of cardiac volume flows in patients may aid in evaluation of the progression of the disease and in determination of clinical options. However, accurate volume flow measurement remains a significant challenge for cardiologists.

Ultrasound may be used to measure volume flow. Doppler ultrasound is a non-invasive and cost effective method for evaluation of intracardiac blood flow and for assessment of cardiac function. With real-time full volume echocardiography, transthoracic 3D color flow imaging (CFI) for every heartbeat may be acquired without stitching such that both mitral valve and LVOT are covered by the color Doppler region of interest. However, flow velocity aliasing may introduce significant errors in flow quantification using color Doppler data. The velocity ambiguity cannot be overcome just by ultrasound data, especially when true velocity is several multiples of the Nyquist level.

BRIEF SUMMARY

By way of introduction, the preferred embodiments described below include methods, instructions and systems for flow quantification in ultrasound imaging. Velocities are unaliased using conditional random fields. To constrain the energy minimization function, a global term includes a measure of a level of aliasing. In one example, the measure of the level of aliasing is based on a change in volume, such as the volume of the left ventricle. The unaliasing is performed along one or more surfaces, such as surfaces intersecting the mitral annulus and the left ventricle outflow tract. The anatomy used may be identified and/or tracked using one or more machine-learnt detectors. Both B-mode and velocity information may be used for detecting and/or tracking the anatomy.

In a first aspect, a method is provided for flow quantification in ultrasound imaging. A transducer is used to ultrasound data representing a cardiac region of a patient. The ultrasound data includes velocity values. A processor calculates a volume change from the ultrasound data, unaliases the velocity values as a function of the volume change and a conditional random field, and calculates a quantity as a function of the unaliased velocity values. The quantity is displayed on a display.

In a second aspect, a system is provided for flow quantification in ultrasound imaging. A beamformer is configured to acquire, using a transducer, data representing a volume of a patient at different times. A detector is configured to detect velocities from the data. A processor is configured to unalias the velocities as a function of spatial constrains and a global consistency term.

In a third aspect, a non-transitory computer readable storage medium has stored therein data representing instructions executable by a programmed processor for flow quantification in ultrasound imaging. The storage medium includes instructions for detecting anatomical information for a heart with a first machine-learned detector, constructing a plane as a function of the anatomical information, tracking the plane with a second machine-learned detector as a function of velocity data and B-mode data, correcting aliasing of the velocity data using conditional random fields within the plane and a global constraint based on a volume change, and calculating a volume flow quantity from the corrected velocity data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF THE DRAWINGS AND PRESENTLY PREFERRED EMBODIMENTS

Volume flow is quantified using ultrasound scanning. First, the anatomical information, such as mitral annulus and left ventricle outflow tract (LVOT), are detected and tracked automatically to account for the heart motion. 3D planes are constructed at the estimated mitral annulus and LVOT locations to sample the color flow data.

The volume flow is quantified from real-time three-dimensional (3D) full volume echocardiography. Real-time 3D volume echocardiography provides high frame rate acquisition of volumetric color Doppler flow images. To overcome an inherent limitation of the color Doppler velocity ambiguity caused by the Nyquist velocity level, a unaliasing process is performed as a conditional random field (CRF) framework with a global consistency potential. The quantification is model-based using conditional random fields with global preferences. The global consistency potential incorporates domain specific prior information based on the instantaneous change in a left ventricle volume.

Figure 1:
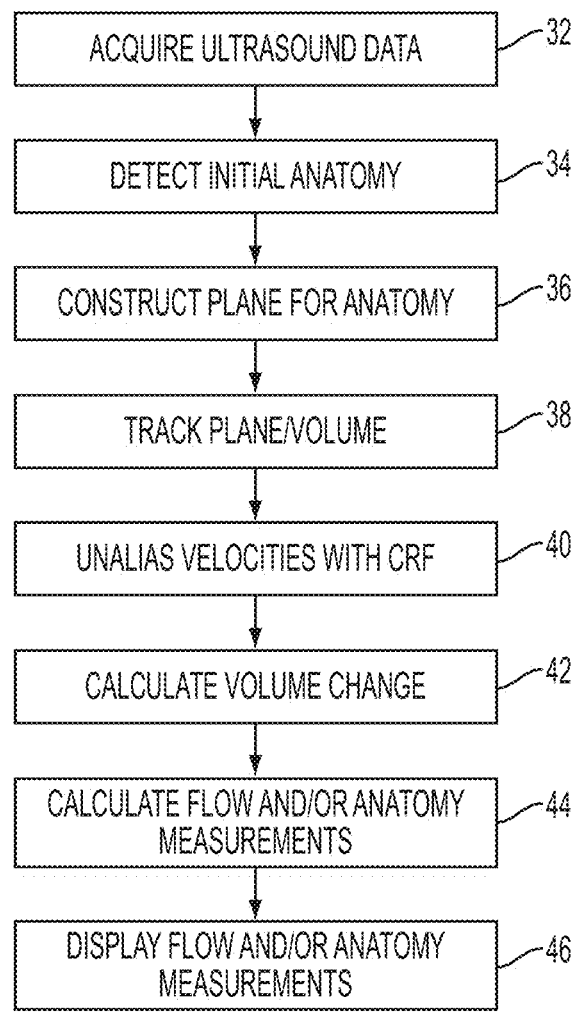
FIG. 1 is a block diagram of one embodiment of a method for flow quantification in ultrasound imaging.

FIG. 1 is a flow chart of one embodiment of a method for flow quantification in ultrasound imaging. In general, anatomy is identified for determining the velocities of interest. The anatomy defines locations for quantifying from velocities. The velocities are unaliased, and the unaliased velocities are used to quantify the volume flow through one or more areas. The unaliasing uses conditional random fields with a global constraint based on an amount of aliasing.

Figure 3:
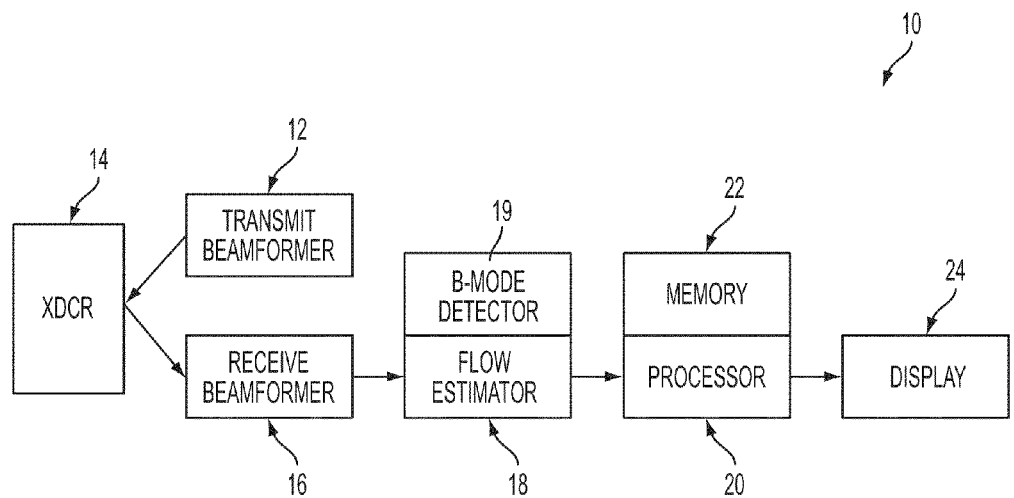
FIG. 3 is a block diagram of one embodiment of a system for flow quantification in ultrasound imaging.

The method of FIG. 1 is implemented using the system 10 of FIG. 3 or a different system. The acts are performed in the order shown or a different order. Different, additional or fewer acts may be provided. For example, acts 34, 36, and 38 are not provided, and the region for unaliasing is based on user input or treated as an entire velocity field of view. As another example, act 46 is not provided. Rather than tracking in act 38, the anatomy may be detected separately for each of different times.

In act 32, medical data representing a volume of a patient is acquired. The data is obtained from memory and/or from ultrasound scanning. The data represents a volume of the patient, such as a cardiac region. Cardiac regions include vessels, veins, and/or the heart. In one embodiment, the left ventricle, other part of the heart, and/or the entire heart of a patient is scanned with ultrasound to acquire the data.

The volume is a three-dimensional region. Data representing voxels or locations distributed throughout the volume is acquired. For example, data for a N×M×O grid where N, M, and O are integer values greater than 1 are acquired. Data for multiple planar slices may represent the volume region. Alternatively, a volume scan is used.

For scanning, an ultrasound transducer is positioned adjacent, on, or within a patient. For adjacent or on a patient, the transducer is positioned directly on the skin or acoustically coupled to the skin of the patient. For within the patient, an intraoperative, intercavity, catheter, transesophageal, or other transducer positionable within the patient is used to scan from within the patient. The user may manually position the transducer, such as using a handheld probe or manipulating steering wires. Alternatively, a robotic or mechanical mechanism positions the transducer.

In one embodiment, a volume scanning transducer is positioned, such as a mechanical wobbler or multi-dimensional array, to scan from a transthoracic or through another acoustic window. The wobbler or multi-dimensional array generates acoustic energy and receives responsive echoes. In alternative embodiments, a one-dimensional array is manually moved for scanning a volume.

For real-time volume scanning, broad beam transmission is used. In response to each broad, planar, or diverging transmission, multiple receive beams are formed. Any scan pattern may be used, such as a single broad transmit beam to cover the entire cardiac region of interest. In alternative embodiments, focused transmit beams are used.

Any mode of scanning may be used. The region includes tissue, fluid, or other structures. Different structures or types of structures react to the ultrasound differently. For example, heart muscle tissue moves, but slowly as compared to fluid. The temporal reaction may result in different tissue velocity or flow velocity data. The shape of a structure or spatial aspect may be reflected in B-mode data. One or more sets of data are obtained, such as obtaining velocity and B-mode (e.g., intensity) sets representing the volume. The B-mode data may be acquired for a larger volume, and the velocity data may be acquired for a sub-volume or region of interest. The ultrasound data corresponds to beamformed data, detected data, and/or scan converted data.

The ultrasound data is acquired to represent the cardiac region at different times. For example, frames of ultrasound data representing the volume are acquired at a ten, fifteen, twenty or other frame rate. Data representing the volume over a part, an entire, or multiple cardiac cycles is acquired.

In act 34, anatomical information is detected. To calculate a quantity, the anatomy associated with the quantity is detected. For example, the three-dimensional location of the left ventricle (LV), including the ventricular wall, the mitral annulus, and the left ventricular outflow tract (LVOT), is automatically detected. Other anatomy may be detected, such as detecting just one or two of the LV, LVOT, and/or mitral annulus. Other valves, chambers, and/or anatomy may be detected.

The detection is in a first, reference, or selected frame representing the volume of the cardiac region. The data representing the volume at a given time is used. The initial detection may be for any time, but is for end systole or end diastole in one embodiment.

Any detection may be used. For example, the user may indicate the anatomy in an image (e.g., trace a mitral annulus and/or left ventricle outflow tract). In one embodiment, the anatomical information is detected automatically or without user input of anatomy position indication. The anatomical information for a heart is detected with one or more image processes or algorithms, such as a manually programmed process.

In one embodiment, one or more machine-learned detectors or classifiers are used to detect the anatomy. Any machine learning may be used. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, about 200 hundred volume sequences representing the heart and including one or more valves are annotated. The annotation indicates valve landmarks and/or surfaces within the volumes. The different anatomies of each volume are annotated. This large number of annotations allows use of machine learning to learn relevant features over a large pool of possible features.

Any features may be used. The features include 3-D Haar, wavelet-like, intensity, steerable, and/or other features. The classifier learns various feature vectors for distinguishing between a desired anatomy and information not being detected. The classifier is taught to distinguish based on the features. Features that are relevant to the anatomies are extracted and learned in a machine algorithm based on the experts' annotations. The training determines the most determinative features for a given classification and discards non-determinative features. Different combinations of features may be used for detecting different anatomies, the same anatomy at different resolutions or times, and/or the same anatomy associated with different translation, rotation, or scale. For example, different sequential classification stages utilize different features computed from the 3D volume data. Each classifier selects a set of discriminative features that are used to distinguish the positive target from negatives.

The data used for the classifier is B-mode data. The features are extracted from the B-mode intensities. In other embodiments, velocity and/or other flow values (e.g., energy or variance) are used instead or in addition to B-mode data. Other types of ultrasound data and/or patient specific non-ultrasound data (e.g., age, weight, and/or cardiac relevant information) may be used.

Once trained, the classifier is used to detect anatomy. By inputting the patient-specific data corresponding to discriminative features, the anatomy model is estimated for a given patient. The locations for the anatomy are estimated for a given time, such as end-diastole, and/or for a sequence of times, such as throughout a heart cycle.

Figure 2A:
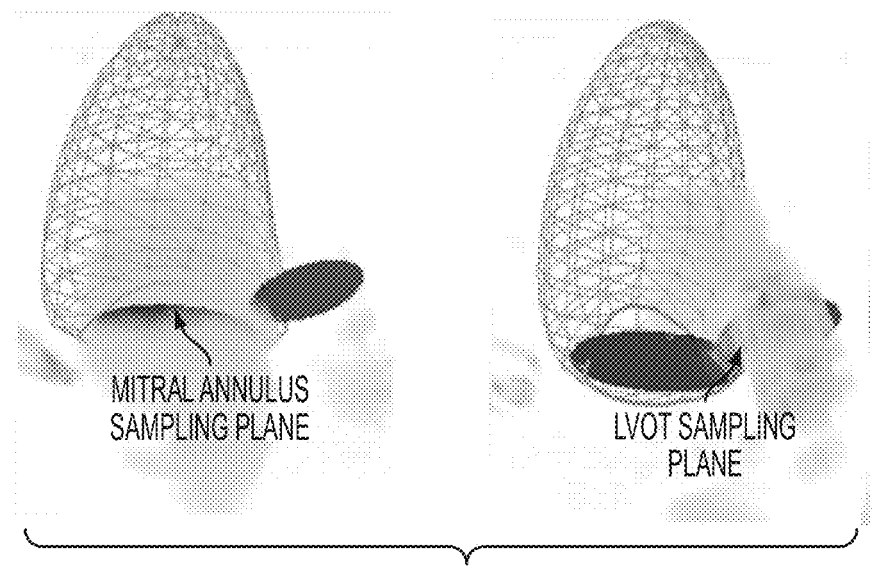
FIG. 2A illustrates an example mesh for a detected left ventricle and associated sampling planes for the mitral annulus and left ventricle outflow tract.

The anatomy model may include a mesh fit to the anatomy, such as the left ventricle (see FIG. 2A). The model outputs the mesh or the mesh is formed based on the locations of anatomy outputted by the model.

In one embodiment, different classifiers or detectors are used for detecting anatomy, refining locations, and tracking anatomy. For example, the left ventricle (LV), the mitral annulus, the left ventricular outflow tract (LVOT), or combinations thereof are detected with marginal space learning (MSL). In the starting or reference frame (e.g., data representing the cardiac region at the end-diastole cardiac phase), the endocardial boundary of the left ventricle, the mitral annulus, and the LVOT are detected. In MSL, the machine-trained marginal space detector learns and performs a hierarchical search. The position is detected first. The orientation at the detected position is then detected. The scale at the position and orientation is then detected. The 3D detector is learned to locate the pose, including the position X=(x, y, z), orientation $\theta=(\alpha, \beta, \gamma)$ and scale S=(sx, sy, sz), of the left ventricle using MSL. Other orders, fewer stages, different stages, and/or additional stages may be used.

In one embodiment, further detection is provided. The output of the MSL is treated as an indication of where to detect. For example, the location provided by the position, orientation, and scale indicate search regions for local estimation of the mitral annulus, left ventricle outflow tract and/or left ventricle. The mesh is locally deformed as the local search is constrained by the detected position, orientation, and/or scale of the left ventricle boundary and/or other anatomy.

The local detection is performed with another machine-trained classifier, but may use other processing instead. For example, a probabilistic booting tree classifier is trained to estimate the local positions. The local deformations of the mitral annulus, the LVOT, and the ventricular wall boundary are estimated based on the posterior distribution $p_t(X|I)$ of each control point on the surface. The surface is the mesh located by MSL, and the control points are the nodes of the mesh. Any feature set may be used for training and detection, such as steerable features.

The probabilistic boosting tree (PBT) unifies classification, recognition, and clustering into one treatment. A probabilistic boosting tree is learned for each anatomy, or a PBT is learned for the group of anatomy locations. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques.

In an alternative embodiment, the detection using the MSL may be considered complete, so the refinement or local detection is not performed. Additional, different, or fewer detectors or classifiers may be used.

In act 36, one or more planes are constructed. The planes are measurement planes or planes used to define regions of interest for further processing. The planes are flat or curved 3D surfaces.

The anatomical information is used to locate one or more surfaces. The planes are constructed at the mitral annulus and the LVOT. For example, a center or single location for each of the mitral annulus and LVOT is located. The surface is defined to pass through the location. Alternatively, the surfaces are detected as part of the anatomy, such as finding three or more points defining the surface.

Figure 2B:
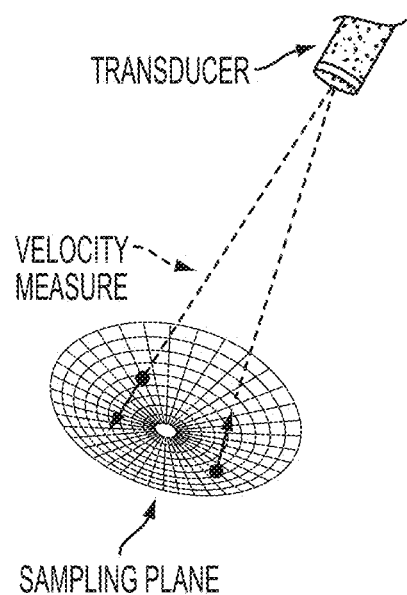
FIG. 2B illustrates a sampling plane as a curved surface relative to a transducer.

The surfaces are oriented. For example, the surfaces have an orientation set relative to the left ventricle and/or the transducer. FIG. 2B shows the measurement surface defined as part of a sphere centered at the tip of the ultrasound pyramid or based on the transducer. The surface is defined in the acoustic space with a constant distance to the transducer. This curved surface corresponds to a sphere in the Cartesian space, centering at the tip of the pyramid (i.e., the transducer).

The spatial extent of the surface is predetermined or based on detected anatomy. For example, the spatial extent is to or just past the left ventricle border or a longest distance from the center of the valve to the left ventricle.

FIG. 2A shows the mitral annulus and LVOT surfaces. Surfaces for different, additional, or fewer anatomical locations may be used.

In one embodiment, the orientation of one or more surfaces is refined. The position, scale, or other information may be refined prior to plane construction as well or instead. The refinement relies on velocity values, but may alternatively or additionally use other data.

To refine the orientation as a function of the velocity values, a two- or three-dimensional distribution of flow at the anatomy of interest is used. The mitral annulus and LVOT have jets or flow regions. The flow at the same time as the reference frame or from another time is used. For example, a cross section through both regions is extracted. The same cross-section, flat plane extends through both regions. The surfaces are reoriented based on the direction of flow from the segmented flow region of the cross-section. The planes are reoriented so that the plane is orthogonal or is more orthogonal to the direction of the jet or flow. The reorientation may be limited, such as providing a range of divergence from orthogonal to the transducer.

Rather than detecting the anatomy and constructing the planes for each frame or time, tracking is used from the initially detected anatomy and constructed planes. In act 38, the anatomy and/or planes are tracked over time. Tracking may ensure temporal consistency and smooth motion and may avoid drifting and outliers. The left ventricle boundary, mitral annulus and/or left ventricle outflow are tracked over time. Alternatively, the detection using the marginal space learning algorithm, probabilistic boosting tree, and/or other detector is repeated for frames of data representing the cardiac region at one or more other phases.

In one embodiment, the planes and/or surfaces are tracked with a machine-learned detector. For example, a Bayesian network of local features and the plane position from another frame are used for tracking. The tracking is performed for each frame t=1, ..., T−1 where T is total number of frames. The data used for extracting features is the B-mode data, velocity data, or combinations thereof. The inputs for a given frame also include the left ventricle and measurement plane locations, $X_{t-1}$, from the previous frame t−1.

In the subsequent frames, the measurement planes are tracked using the Bayesian approach. The Bayesian function is represented as:

$$\arg\max \text{ of } X_t p(X_t|Y_{1:t}) = \arg\max \text{ of } X_t p(Y_t|X_t) p(X_t|Y_{1:t-1})$$

where $Y_{1:t}=(Y_1, \ldots, Y_t)$ are the local features and image templates from the first t frames $I_{1:t}=(I_1, \ldots, I_t)$. The image template is the prior plane and/or anatomy locations. $X_t$ is used to denote a concatenation of the mesh point positions, $X_t=[X_1, \ldots, X_n]$, which are estimated at the current time instance t, and n is the total number of points in the model. This Bayesian function is solved using any optimization technique.

Starting from the detection result at the initial frame, the model deformations are propagated to neighboring frames using both the learned features and the local image templates. The tracking indicates the location of the planes at different times.

The tracking is refined in one embodiment. For example, a mean shift algorithm is used for local refinement. Based on the mitral annulus and LVOT locations obtained from the tracking, a local refinement places the measurement planes accurately using the mean shift approach. The plane is shifted to provide the maximum flow. Mean shift finds the maxima of a density function given velocities sampled from the region of interest. The shift is performed in an iterative manner by translation and/or rotation. As a result, the areas associated with volume flows are computed consistently based on the anatomical structure of the left ventricle.

The anatomy, regardless of how detected, is used to calculate a flow quantity. For example, the volume of flow through the mitral annulus and/or LVOT is calculated. The volume of flow is based on velocity through an area. The area is defined by the measurement planes. The velocities along the measurement planes are used to calculate the volume of flow.

The velocities may be aliased. In color flow images, aliasing is a common issue which describes single or multiple exceeding of the color Doppler Nyquist velocity, causing ambiguity for velocities beyond the Nyquist level. Due to the setting of the pulse repetition interval, higher velocities may wrap around as different values. To avoid inaccuracies associated with aliasing, the velocities are unaliased in act 40. In preparation for unaliasing, an indication of the amount of aliasing is determined. The change in volume of the left ventricle may be used to determine the indication of the level of aliasing.

In act 40, the velocity values along the planes are automatically unaliased by a processor. The unaliasing operation is repeated for each plane at each time. The unaliasing is independent for each time and plane, but may use information from other times and/or planes in other embodiments. Any aliased velocity values are unaliased along the measurement surfaces for inflow, outflow or both inflow and outflow regions of the left ventricle or other chamber. For example, the velocities in each frame (i.e., each time) are unaliased for the surface of the mitral annulus and for the surface of the LVOT. Velocity values that are not aliased remain the same or are not unaliased. Velocity values for other locations not on the surface are not altered, but may be altered. For example, velocities are unaliased for a three-dimensional color flow region of interest.

The unaliasing is performed as a function of the volume change and a conditional random field. To recover the underlying velocity values from the aliased measurements, a conditional random field (CRF) model is built for each of the flow sampling surfaces or other locations. Given the color flow data (i.e., velocities), $v_i^{(t)}$ (i in V), sampled on the measurement planes, the unaliasing factor $f_i^{(t)}$ for each sampling point (e.g., for each velocity representing the surface) is determined. The unaliasing factor represents an amount of change in the velocity or amount of aliasing. The unaliasing factor is a non-negative integer (e.g., between 0 and 2) representing the number of aliasing transitions (e.g., 0 represents an unaliased velocity, 1 represents aliasing by a single cycle, and 2 represents aliasing by two cycles). Alternatively, the unaliasing factor is a different representation of the amount of change or the correct velocity.

The unaliasing factor is formulated as a conditional random field (CRF) model $G=(V,\epsilon)$, where the set V is used for indexing random variables associated with each sampling point, $v_i^{(t)}$, and $\epsilon$ is the set of undirected edges between nodes or sampling points representing compatibility relationships between random variables. $\epsilon$ is pair-wise or only edges between spatially adjacent (e.g., connected) nodes are used, but more complex edges may be used. The unaliasing factor $f_i^{(t)}$ is the corresponding label for each node or random variable. The energy function of graph G is written as the sum of unary and smoothness potentials, respectively:

$$\Sigma \phi(f_i^{(t)}) + \Sigma \psi(f_i^{(t)}, f_j^{(t)})$$

where $\Sigma \phi(f_i^{(t)})$ is the unary data term from i in the set of V and $\Sigma \psi(f_i^{(t)}, f_j^{(t)})$ is the smoothness potential from i, j in the set of $\epsilon_L$. V are the indices associated with each sampling point, and the set of local edges $\epsilon_L$ is the pair-wise connection between the local nodes (e.g., the nodes of the mesh or sampling pattern on the surface). To simplify the notation, the frame index $^{(t)}$ is not used below.

The data term $\phi(f_i)$ encodes agreement between a label $f_i$ and the color flow data $v_i$. The data term may be modeled as a Gaussian distribution:

$$\phi(fi) = \frac{1}{\sqrt{2\pi\sigma_i^2}} e^{-\frac{(v_i + v_s f_i - \mu_i)^2}{2\sigma_i^2}}$$

where $v_s$ is the color Doppler Nyquist velocity. The two parameters, mean $\mu_i$ and standard deviation $\sigma_i$, are learned from a training set for the given surface. Other models may be used.

The pair-wise spatial term $\psi(f_i, f_j)$ encourages the spatial smoothness between neighboring nodes $f_i$ and $f_j$. For simplicity, the spatial term is modeled as a zero mean Gaussian distribution:

$$\psi L(f_i, f_j) = \frac{\lambda L}{\sqrt{2\pi\sigma_{ij}^2}} e^{-\frac{(f_i + f_j)^2}{2\sigma_{ij}^2}}$$

where $\lambda_L$ is a weighting factor. The weighting factor is learned from the training dataset. Other models may be used.

There is an inherent ambiguity as each label $f_i$ may choose an arbitrary number, which might lead to an invalid flow volume. To deal with the ambiguity, a global constraint is introduced into the energy equation used for the conditional random field solution. The energy of the conditional random field includes the data term, the spatial term, and the global term. The global constraint is a global consistency potential incorporating domain specific prior information.

Domain-specific knowledge is be leveraged to remove this ambiguity. The LV volume change and the volume flow measure the same amount of blood flow through the left ventricle at a certain time instance (e.g., over a same period). The LV volume change between neighboring frames or other frames for the period is introduced to remove the ambiguity of the unaliasing factor estimation and consequently to increase the robustness of cardiac flow volume quantification. Other measures than the change in volume or change in left ventricle volume may be used.

In act 42, the volume change of the left ventricle is calculated. The calculation is from the ultrasound data, such as from B-mode data. The left ventricle is detected and tracked, so the surface of the left ventricle at different times is known. The change in volume between the two times is determined by a processor. Given the tracked LV endocardial boundaries in the previous frame t−1 and the current frame t, the corresponding LV cavity volumes are calculated as $V_{t-1}$ and $V_t$, respectively. The LV volume change is calculated as $dV_t = V_t - V_{t-1}$. Any two times may be used, such as between adjacent frames in time.

The volume change is used to estimate a level or amount of aliasing present in the velocity values. The average number of aliased velocities is computed as:

$$f_g = \left\lfloor \frac{dV_t \cdot f_r}{\sum_i dA_i \cdot v_s} \right\rfloor$$

where $f_r$ is the frame rate, $dA_i$ is the area of each sampling point, and $v_s$ is the color Doppler Nyquist velocity. $f_g$ is a discrete value as the floor function $\lfloor . \rfloor$ returns the largest non-negative integer not exceeding the value. Other measures may be used.

Adding the global term to the energy function of the conditional random field provides:

$$\sum_{i \in V} \phi(f_i) + \sum_{(i,j) \in \epsilon_L} \psi L(f_i, f_g) + \sum_{(i,g) \in \epsilon_G} \psi G(f_i, f_g)$$

where $\psi_G(f_i, f_g)$ is the global consistency potential and $\epsilon_G$ is the set of global edges. The set of local edges $\epsilon_L$ is the pairwise connection between the local nodes, and the set of global edges $\epsilon_G$ connects the global latent node with each of the local nodes.

The global potential $\psi_G(f_i, f_g)$ enforces the global consistency for each node. The global preference $f_g$ is computed based on the LV cavity volume change. This global preference is incorporated in the global potential as:

$$\psi G(f_i, f_g) = \frac{\lambda G}{\sqrt{2\pi\sigma_i^2}} e^{-\frac{(f_i + f_g)^2}{2\sigma_i^2}}$$

where $\lambda_G$ is a weighting factor, which is learned from the training dataset. Other models may be used.

Using the conditional random fields and the energy function, the unaliasing factor is determined for each node of a given surface. A solution of the energy function with a minimum energy across the surface or set of locations to be unaliased is determined. The unaliasing factors resulting in the minimum energy for the surface are determined. By minimizing the energy with the global term, the ambiguity is removed, providing an accurate indication of the unaliasing.

Any optimization, search pattern, or solution approach may be used to solve the conditional random field. For example, an iterative solution attempts various combinations of unaliasing factors. The next combination is selected based on trends or other information from other attempts. The solution occurs when a global or local minimum or sufficiently low relative energy is identified.

Based on the unaliasing factors, the velocity values along the surface for a given time are unaliased. The velocity values are corrected to account for the amount, if any, of aliasing. The result is a set of velocities corresponding to the minimum energy of the conditional random field.

In act 44, a quantity is calculated as a function of unaliased velocity values. Any quantity may be calculated by the processor. For example, an average velocity, peak velocity, velocity per area, variance of velocity over space and/or time, or other value is calculated.

In one embodiment, the volume flow is calculated. The volume flow is a measure of the fluid volume passing through an area over a time period. For example, the area of the mitral annulus is multiplied by the velocity average of the area, summed over each time increment for a desired period. As another example, the volume flow, $Vf_t$ is computed from the corrected velocity data as:

$$Vf_t = \Sigma v'_i * dA_i^{(t)} * dt$$

where v' is the estimated velocity after unaliasing, $dA_i^{(t)}$ is the unit area of each sampling point, and dt is the time increment. To compute the volume of the mitral inflow and the LVOT outflow, the areas enclosed by the mitral annulus and the LVOT ring are used based on sample points with sufficient velocity or flow.

Other measures of the volume passing through an area as a function of time may be used. The same quantity may be calculated for the LVOT. The difference between the volume flow for the mitral annulus and the LVOT may be calculated as a measurement of mitral regurgitant volume.

In one embodiment, the velocity values are further corrected for the scan angle. Ultrasound scanning measures the velocity along a scan line, so is the velocity to or from the transducer. When the flow is in a different direction, the estimated velocity value may be lower than the actual velocity of the flow. Where the transducer is oriented to scan along a line orthogonal to the area of flow being measured, the velocities reflect flow along the desired vector. Where the acoustic window results in another angle, the velocities may be corrected or used to determine the flow along the desired direction. A direction of flow is determined, such as from user input, boundary analysis, or other source. The velocity is corrected based on the angle of difference between the scan line and the direction of flow.

In act 46, the quantity is displayed on a display. The quantity may be displayed as a value, such as a numerical value. Alternatively or additionally, the quantity is displayed in a graph. For example, a graph of volume flow over time is generated. The volume flow between pairs of frames or volumes is calculated and graphed to show volume flow over time.

The quantity may be displayed with a two or three-dimensional image. For example, the B-mode, velocity, other data, and/or combinations thereof is rendered using three-dimensional rendering. A multiplanar reconstruction may be generated from the data. An image of the measuring surface may be generated. An image of the model or detected anatomy (e.g., of the mesh) may be generated.

One or more two- and/or three dimensional images may be generated and displayed at a same time. A sequence of images may be generated to show the anatomy over time.

Where the image uses velocity values, the corrected velocities are used. As a result, little or no aliasing is shown. The image values are directly or indirectly mapped from the unaliased velocity data. For example, color values correspond to the amplitude of the velocity values. In another example, the image values correspond to a combination of different data, such as phase velocity values and B-mode information. As another example, the color values correspond to a magnitude and/or orientation of a velocity vector derived from the velocity values.

The unaliased velocity values may be used for other purposes than imaging or quantity calculation. In one embodiment, one or both of the velocity scale and imaging frequency are set as a function of the results of the unaliasing. The pulse repetition interval or other velocity scale characteristic is calculated from the unaliased velocities. The pulse repetition interval provides a minimum velocity scale that does not alias. By finding a maximum velocity, the scale may be set to include the maximum. Baseline, parameters for auto-Doppler tracking, persistence, spatial filters, thresholds, and/or clutter filters may be set.

FIG. 3 shows one embodiment of a system 10 for flow quantification in ultrasound imaging. The system 10 includes a transmit beamformer 12, a transducer 14, a receive beamformer 16, a flow estimator 18, a B-mode detector 19, a processor 20, a memory 22, and a display 24. Additional, different or fewer components may be provided. For example, one or more of the components, such as the processor 20 and/or the flow estimator 18, are in a workstation separate and remote from the beamformers and transducers. As another example, the processor 20 is integrated within the flow estimator 18 or not provided separately. Where the system 10 is a medical diagnostic ultrasound imaging system, further components connect with the processor 20 or flow estimator 18, including a scan converter and/or a rendering processor.

The components are configured by hardware and/or software. Firmware, design, or other instructions or tables may be used to configure one or more of the components.

The transmit beamformer 12 generates transmit waveforms for a plurality of channels. Due to relative timing and apodization of the waveforms across the transducer array 14, one or more transmit beams are generated. Plane wave, divergent waves, or other broad beam generations may alternatively be used. The transmissions are separated by a pulse repetition interval, resulting in pulses being transmitted at a pulse repetition frequency.

In response to each transmission, the receive beamformer 16 applies relative delays and apodization to form samples representing one or more regions of a patient. Each sample is associated with a particular time based on the pulse repetition interval. The receive beamformer 16 generates radio frequency or in-phase and quadrature data for each sample.

The transmit and receive beamformers 12, 16, using the transducer 14, acquire data representing a volume of a patient at different times. Any scan format may be used, such as scanning along multiple planes in sector, Vector™, or linear format. Other three-dimensional scan formats may be used. The transducer 14 is one or multi-dimensional array of elements for electronically and/or mechanically (e.g., wobbler or hand held) scanning the volume of the patient.

Using broad beam transmission and receiving along multiple (e.g., sixteen or more) receive beams in response to each transmission, the volume may be scanned at a greater frame rate. For estimating velocity for a give time, multiple scans of the same locations are performed in succession. A single scan and/or scans for one repetition for velocity estimation may be used for B-mode scanning. By acquiring ongoing sets of data, a moving window may be used to provide velocities at different times. Sets or frames of data representing the volume at different times (e.g., 3D+t sets) are acquired. Any frame rate may be used, such as 10, 15, 20, 22, or more volumes per second.

The flow estimator 18 is a detector for estimating velocity. For example, the flow estimator 18 is a Doppler processor, general processor, digital signal processor, application specific integrated circuit, correlation processor, digital circuit, analog circuit, combinations thereof, or other now known or later developed device for determining or estimating flow characteristics. A clutter filter for minimizing low velocity tissue may be included. The flow estimator 18 estimates velocities, energy, and/or variance from the sequence of signals representing a same location at different times. For a Doppler processor, the phase of the first lag of the autocorrelation function of the in-phase and quadrature components indicates the Doppler frequency shift, and the frequency shift information is converted to velocity information. The magnitude of the zeroth lag of the autocorrelation function provides energy.

The scale or range of velocities determined by the flow estimator 18 is subject to the Nyquist sampling frequency, so the pulse repetition interval or pulse repetition frequency limits the velocity scale. Increasing the pulse repetition frequency allows for a larger scale, but less low motion sensitivity. Where the velocity scale has a small range in comparison to the velocities of the flow being imaged (i.e., under sampling), some velocity values may be aliased, resulting in incorrect estimation of velocity. A $+/-2\pi$ wraparound phase error aliases some velocity data, such as high positive or high negative velocities.

The B-mode detector 19 is a digital signal processor, processor, application specific integrated circuit, digital circuit, analog circuit, combinations thereof, or other now known or later developed device for determining the intensity of ultrasound response. The intensity is a power or energy of an acoustic echo for each sample location. For example, the sum of the square of the in-phase and the square of the quadrature components is determined. The dynamic range of the B-mode values may be compressed, such as converted to a log scale.

The processor 20 is a general processor, a control processor, a digital signal processor, an application specific integrated circuit, a field programmable gate array, a graphics processing unit, a digital circuit, an analog circuit, combinations thereof or other now known or later developed device. In one embodiment, the processor 20 is a single processor. The processor 20 may include multiple different processors implementing the same function in parallel or different functions in series. While shown as a separate device, the processor 20 may be implemented as a control or other processor within different components, such as a processor of the flow estimator 18, transmit beamformer 12, receive beamformer 16, a control processor for the system 10, or other now known or later developed processor within the system 10.

The processor 20 is configured to detect anatomy and/or locations used for calculating a quantity. Any detection may be used, such as using one or more machine-learnt detectors. For example, the processor 20 locates and tracks the left ventricle as a function of B-mode data and velocities. The detection and tracking may use one or more machine-learnt matrices, classifiers, and/or detectors. B-mode data is used to determine the anatomical locations, and velocities are used to refine the locations and/or orient a region of interest relative to the anatomy. In alternative embodiments, the user indicates the position on an image. The processor 20 determines the position based on the user input.

The processor 20 is configured to unalias velocities. Some velocities may be aliased and others may not. To unalias, whether a given velocity is aliased and by how much is determined. Any aliasing, at least of velocities in a region of interest, are corrected.

The velocities are unaliased as a function of spatial constrains and a global consistency term. A conditional random field function is used to determine the unaliased velocities. The energy of the conditional random field is a function of a global consistency term and spatial constraints. Unary (node), smoothess (edge), and the global consistency term are used in the energy function. Any combination of the terms and/or models for the terms may be used to create the energy function.

The global consistency term is a function of a measure of alias level of the velocities, and the spatial constraint is a pair-wise term. In other embodiments, the global consistency term is a selection of a known accurate (non-aliased) velocity in the field of view. Using the velocities themselves for node or unary terms, an optimized solution minimizing the energy is determined.

The processor 20 is configured to calculate a quantity from the unaliased velocities. Any quantity may be calculated, such as a volume flow. The processor 20 may generate an image. The image is of a value, such as of the quantity, of a graph, and/or of anatomy in a plane or volume.

The display 24 is a CRT, LCD, projector, plasma, printer, combinations thereof or other now known or later developed device for outputting an image representing the quantity, velocity distribution, and/or anatomy. The display 24 generates an image representing velocities or other motion values. The image includes colors corresponding to the image values. The image may be a combination of B-mode or other imaging mode data with the velocity data. For example, the velocity image values overlay or overwrite B-mode data within a region of interest. As another example, the velocity image values and other data are combined, such as combining by averaging, weighted averaging or another function. The combination of velocity values with other data may be performed prior to mapping to the image values.

The memory 22 stores ultrasound data (e.g., velocity values and/or B-mode data), detected anatomy, locations, a mesh, tracking information, one or more calculated quantities, energy function, energy calculations, or other processed information.

While the memory 22 is shown as a separate component, any of the components of the system may include the memory 22. The component is a programmed processor operable to implement instructions stored in the memory. For example, instructions are stored in a common memory for implementing processes by different processors or are stored as separate programs for implementing the different processes of each component. The instructions are for flow quantification in ultrasound imaging. For example, the storage medium includes instructions for correcting velocity values with a unaliasing factor. Under sampled velocity values based on the pulse repetition interval are unwrapped to provide low motion sensitivity with minimal or no aliasing.

The instructions for implementing the processes, methods and/or techniques discussed above are provided on the non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 4:
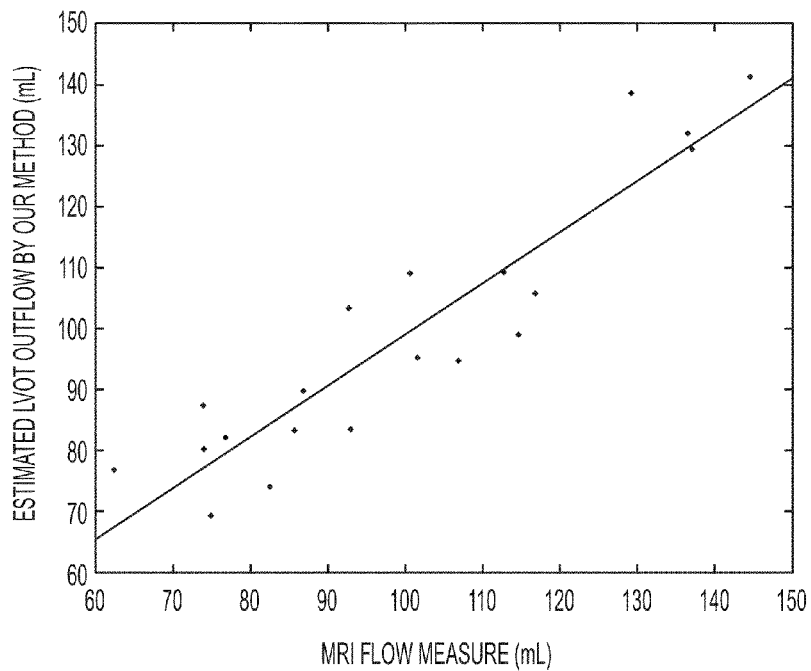
FIG. 4 is an example graph showing volume flow from ultrasound as compared to volume flow from magnetic resonance imaging (MRI).

FIG. 4 shows a comparison between (1) the volume flow estimated by detection and tracking of anatomy with ultrasound data and unaliasing and (2) phase-contrast (PC) flow measurements using magnetic resonance imaging (MRI). The vertical axis is the unaliased LVOT outflow based on the sampled color Doppler data. The anatomy is detected by MSL, with local deformations using PBT, and refinement of surface orientation using velocities. The detected anatomy is tracked using a Bayesian function and refined using the mean shift. The unaliasing is performed using the conditional random fields with a global consistency term based on the change in left ventricle volume.

The measurements are performed on 20 patients in this example. The correlation between estimated flow volumes and the MRI measurements has a high score of 0.93, which demonstrates the accuracy and robustness of the ultrasound-based measures.

Using the machine-learnt classifiers for initial detection, local deformation, and tracking and using the unaliasing with conditional random fields including a global constraint term, the volume flow may be efficiently calculated. For example, the quantity is calculated at 0.2 second per volume of ultrasound data. More rapid or slower performance may be provided.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and the scope of this invention.

We claim:

1. A method for flow quantification in ultrasound imaging, the method comprising:
   acquiring, with a transducer, ultrasound data representing a cardiac region of a patient, the ultrasound data comprising velocity values of flow of fluid in the cardiac region of the patient;
   calculating, with a processor of an ultrasound imaging system, a volume change from the ultrasound data;
   unaliasing, with the processor of the ultrasound imaging system, the velocity values as a function of the volume change and a conditional random field;
   calculating, with the processor of the ultrasound imaging system, a quantity as a function of the unaliased velocity values; and
   displaying, on a display, the quantity.

2. The method of claim 1 wherein acquiring comprises acquiring the velocity values for the cardiac region, where the cardiac region comprises a volume of the heart.

3. The method of claim 1 wherein acquiring comprises also acquiring B-mode data representing the cardiac region at different times, and wherein calculating the volume change comprises calculating the volume change with the B-mode data.

4. The method of claim 3 wherein calculating the volume change comprises calculating a left ventricle volume change.

5. The method of claim 1 wherein unaliasing comprises estimating a number of aliased velocities, and including a global constraint in an energy function conditional random field, the global constraint being a function of the number.

6. The method of claim 1 wherein unaliasing comprises determining a set of velocities with a minimum energy of the conditional random field.

7. The method of claim 6 wherein an energy of the conditional random field comprises a data term that is a function of the velocity values, a spatial pair-wise term, and a global term.

8. The method of claim 1 wherein unaliasing comprises unaliasing the velocity values along one or more surfaces for an inflow, an outflow, or both inflow and outflow regions.

9. The method of claim 1 wherein calculating comprises calculating a volume flow.

10. The method of claim 1 wherein displaying comprises displaying the quantity with an image of the cardiac region.

11. The method of claim 1 wherein acquiring comprises acquiring B-mode information;
further comprising:
 detecting a position, orientation, and scale of a left ventricle boundary with a machine-trained marginal space detector;
 estimating a mitral annulus and left ventricle outflow tract with a machine-trained probabilistic boosting tree classifier, the probabilistic boosting tree classifier using a local search constrained by the detected position, orientation, and scale of the left ventricle boundary;
wherein calculating comprises calculating as a function of the left ventricle boundary; and
wherein unaliasing comprises unaliasing in a first surface intersecting the mitral annulus and in a second surface intersecting the left ventricle outflow tract.

12. The method of claim 11 further comprising:
refining the orientation as a function of the velocity values.

13. The method of claim 1 further comprising:
detecting a left ventricle boundary, a mitral annulus, and a left ventricle outflow track;
tracking the left ventricle boundary, mitral annulus and left ventricle outflow track over time with a Bayesian network of local features and plane position.

* * * * *